(12) United States Patent
Freer et al.

(10) Patent No.: US 11,439,638 B1
(45) Date of Patent: Sep. 13, 2022

(54) DRUG AND DIAGNOSTIC COMBINATION SYSTEM TO IDENTIFY AND TREAT SINGLE-STRANDED RNA VIRUSES INCLUDING CORONAVIRUSES

(71) Applicant: AiPharma Global Holdings LLC, Lewes, DE (US)

(72) Inventors: Carl Johan Freer, Bloomfield Hills, MI (US); Richard Kaszynski, Tokyo (JP); Alessandro Gadotti, Rome (IT)

(73) Assignee: Feynman Labs, LLC, Dubai (AE)

( * ) Notice: Subject to any disclaimer, the term of this patent is extended or adjusted under 35 U.S.C. 154(b) by 0 days.

(21) Appl. No.: 17/565,675

(22) Filed: Dec. 30, 2021

Related U.S. Application Data

(60) Provisional application No. 63/253,084, filed on Oct. 6, 2021.

(51) Int. Cl.
| | | |
|---|---|---|
| *A61K 31/4965* | (2006.01) |
| *A61K 31/7048* | (2006.01) |
| *G01N 33/569* | (2006.01) |
| *A61P 31/14* | (2006.01) |

(52) U.S. Cl.
CPC ...... *A61K 31/4965* (2013.01); *A61K 31/7048* (2013.01); *A61P 31/14* (2018.01); *G01N 33/56983* (2013.01); *G01N 2333/165* (2013.01)

(58) Field of Classification Search
CPC .. A61K 31/4965; A61K 31/7048; A61P 31/14
See application file for complete search history.

(56) References Cited

PUBLICATIONS

Channappanavar et al. "Pathogenic human coronavirus infections: causes and consequences of cytokine storm and immunopathology," Semin. Immunopathol. 2017, vol. 39, pp. 529-539 (Year: 2017).*

Saha et al. "Discovering Potential RNA dependent RNA polymerase inhibitors as prospective Drug against Covid-19: An in silico Approach," Frontiers in Pharmacology, Feb. 2021, vol. 12, Article 634047), particularly, the abstract at p. 1. (Year: 2021).*

Portmann-Baracco et al. "Antiviral and anti-inflammatory properties of ivermectine and its potential use in Covid-19," Arch Bronconeumol. 2020; 56; 831 (Year: 2020).*

Principle Trial "Favipiravir to be investigated as possible Covid-19 treatment for at home recovery in the Principle trial," Apr. 2021, https://www.principletrial.org/news/favipiravir-to-be-investigated-as-a-possible-covid-19-treatment-for-at-home-recovery-in-the-principle-trial (Year: 2021).*

Hassanipour et al. "The efficacy and safety of Favipiravir in treatment of Covid-19: a systematic review and meta-analysis of clinical trials," Natural Portfolio, May 13, 2021 https://www.nature.com/articles/s41598-021-90551-6.pdf) (Year: 2021).*

Andryukov "Six decades of lateral flow immunoassay: from determining metabolic markers to diagnosing Covid-19" AIMS Microbiology, 2020, vol. 6, No. 3, pp. 280-304. (Year: 2020).*

* cited by examiner

*Primary Examiner* — Shengjun Wang
(74) *Attorney, Agent, or Firm* — Inventa Capital PLC

(57) ABSTRACT

A method for treating an early-stage microbial infection comprising determining whether a subject exposed to a coronavirus, such as SARS-CoV-2, or suspected of being exposed to a microbe, or exposed to another infected with or suspected of being infected with a coronavirus and, if the subject is infected with the coronavirus, administering an antimicrobial agent is provided herein.

12 Claims, No Drawings

US 11,439,638 B1

DRUG AND DIAGNOSTIC COMBINATION SYSTEM TO IDENTIFY AND TREAT SINGLE-STRANDED RNA VIRUSES INCLUDING CORONAVIRUSES

CROSS-REFERENCE TO RELATED APPLICATION

This application claims the benefit of U.S. Provisional Application No. 63/252,084, filed Oct. 6, 2021. The entire disclosure of the above application is incorporated herein by reference.

FIELD

The present disclosure generally relates to a diagnostic and treatment of microbial infections, particularly infections from the coronavirus.

BACKGROUND

This section provides background information related to the present disclosure which is not necessarily prior art.

The novel severe acute respiratory syndrome coronavirus 2 (SARS-CoV-2) was identified in 2019 and has since spread across the world. It is present in every virtually country and has been declared a pandemic by the World Health Organization (WHO). Those infected with SARS-CoV-2 may develop coronavirus disease (COVID-19). Due to its rapid expansion, humans have yet to develop a natural herd immunity to the virus. Although three vaccines have been approved in the United States to combat SARS-CoV-2, treatment options remain limited. Current treatments include monoclonal antibody treatments (e.g., casirivimab and imdevimab), antivirals (e.g., remdesivir), immunomodulators (e.g., dexamethasone), oxygenation, ventilation, and supportive care.

Ivermectin was developed by Merck in the 1980s and is FDA-approved to treat parasitic infections (such as strongyloidiasis). In addition to its anti-parasitic effects, ivermectin has been shown to inhibit dengue virus and yellow fever virus. (Xu, et al., *PLoS Negl Trop Dis.*, 2018; Mastrangelo, et al. *J Antimicrob Chemother,* 2012.) Recently, ivermectin has been shown to slow replication of SARS-CoV-2 in mammalian cells, in vitro. (Caly, et al., *Antiviral Res.*, 2020.) However, it is unclear whether ivermectin by itself is effective for treating or preventing COVID-19, in vivo. (Popp, et al. *Cochrane Database Syst Rev,* 2021.)

Favipiravir is a broad-spectrum inhibitor of viral RNA-dependent RNA polymerase and is sold under brand names such as Avigan, Avifavir, Areplivir, FabiFlu, Favipira, Qifenda, and Reeqonus. In vivo, favipiravir is phosphorylated to its active form, favipiravir-RTP. Favipiravir and favipiravir-RTP are known to be effective against influenza viruses, arenaviruses, bunyaviruses, and filoviruses. (Furuta, et al., *Proc Jpn Acad Ser B Phys Biol Sci,* 2017.) Favipiravir's effect on SARS-CoV-2 or its efficacy for treating COVID-19 remains undetermined. (Hassanipour, et al., *Sci Rep.,* 2021.)

In an in vitro study in Vero E6 or Calu-3 cells, the combination of ivermectin and favipiravir showed a synergistic antiviral effect (as measured by reduced $IC_{50}$ values). However, the in vitro synergistic effect has not been replicated or validated in an in vivo setting. (Jitobaom, et al., Research Square, 2021.)

SUMMARY

This section provides a general summary of the disclosure, and is not a comprehensive disclosure of its full scope or all of its features.

One embodiment described herein is a method for treating early-stage infection by a microbe, such as a virus, comprising the steps of obtaining a sample from a subject, providing the sample to a lateral flow assay, determining whether the subject is infected with the microbe, and, if the subject is so infected, treating the subject with an antimicrobial agent, such as an antiviral agent. In some embodiments, the subject is exposed has been exposed to the virus, is suspected of having been exposed to the virus, or has been in contact with a person exposed to or suspected of being exposed to the virus.

DETAILED DESCRIPTION

The description included herein are intended for purposes of illustration only and are not intended to limit the scope of the present disclosure.

I. Definitions

At the outset, in the context of the present disclosure, the following is provided for reference with regard to various terms and/or abbreviations and/or descriptions herein.

As used herein, the term "microbe" refers to one or more organisms that infect a body and may cause illness. Microbes are generally known in the art and include viruses, bacteria, fungus, and parasites. Viruses include the family of coronaviruses, which includes SARS-CoV-2, which is responsible for COVID-19. Additional viruses include, but are not limited to, the influenza virus, severe fever with thrombocytopenia syndrome (SFTS) virus, ebola virus, and Lassa virus.

As used herein, the term "antimicrobial agent" refers to compound or composition which is effective in killing, inhibiting the replication of, inhibiting infectivity of, and/or inhibiting the growth of one or more microbes. The antimicrobial agent includes antiviral agents, antibacterial agents (e.g., antibiotics), and antifungal agents. Antiviral agents described herein are not particularly limited and include agents effective in killing and/or inhibiting the replication, infectivity, and/or growth of one or more viruses. The antiviral agent may be a purine nucleic acid analog, such as an inhibitor of RNA-dependent RNA polymerase (RDRP). Antiviral agents include, but are not limited to, favipiravir, favipiravir-RTP, remdesivir, and molnupiravir. Antibacterial agents described herein are not particularly limited and include agents effective in killing and/or inhibiting the replication, infectivity, and/or growth of one or more bacteria. Antibacterial agents include, but are not limited to, amoxicillin, doxycycline, cephalexin, ciprofloxacin, clindamycin, metronidazole, sulfamethoxazole and trimethoprim, amoxicillin and clavulanate, levofloxacin, and azithromycin. Antifungal agents described herein are not particularly limited and include agents effective in killing and/or inhibiting the replication, infectivity, and/or growth of one or more fungi. Antifungal agents include, but are not limited to, clotrimazole, econazole, miconazole, terbinafine, fluconazole, ketoconazole, nystatin, amphotericin, and ketoconazole.

As used herein, the term "early-stage infection" refers to a stage of infection with a microbe wherein the subject does not present with symptoms associated with infection by the microbe. For example, a subject would be considered having an early-stage infection with SARS-CoV-2 after having been exposed to the virus but before presenting with symptoms associated with COVID-19 and/or a SARS-CoV-2 infection. The subject may be considered asymptomatic. Alternatively, a subject may be considered in an early-stage infection if the subject presents with symptoms of SARS-CoV-2 infection are indistinguishable from symptoms of infection from other microbes.

As used herein, a "lateral flow assay" refers to an assay that confirms the presence or absence of an analyte (e.g., an antigen of interest) in a sample, such as a biosample from a subject. The lateral flow assay is described in U.S. Pat. No. 8,399,261, which is incorporated herein by reference. The antigen utilized in the lateral flow assay may be from a microbe, such as a virus (e.g., SARS-CoV-2) that has infected the subject.

As used herein, a "sample" refers to, for example, a biosample, obtained from the subject for use in the lateral flow assay. The sample is not particularly limited so long as it can be used in the lateral flow assay. The sample may be selected from the group consisting of saliva, blood, plasma, lymph, mucus, urine, feces, cells, and tissues.

As used herein, the term "combination" refers to an association of two or more active agents. As used herein, a combination comprises an antiviral agent and an antiparasitic agent. Combination encompasses separate formulations, such as where the antiviral agent and the antiparasitic agent are provided in separate dosage forms, such as in a kit. Alternatively, the combination encompasses a single formulation, such as when the antiviral agent and the antiparasitic agent are provided in a single composition, including but not limited to, a tablet, capsule, caplet, solution, suspension, and emulsion.

As used herein, the term "antiparasitic agent" is distinguished from the general term "antimicrobial agent" in that it is an agent, compound, or composition which is effective in killing and/or inhibiting the reproduction, growth, or infectivity of one or more parasites. The antiparasitic agent includes avermectins, which are compounds comprising a 16-membered macrocyclic lactone. Avermectins include ivermectin, selamectin, doramectin, eprinomectin, and abamectin. Alternatively, the antiparasitic agent includes nitazoxanide, melarsoprol, eflornithine, metronidazole, tinidazole, miltefosine, mebendazole, pyrantel pamoate, thiabendazole, diethylcarbamazine, niclosamide, praziquantel, albendazole, praziquantel, rifampin, amphotericin B, and fumagillin.

As used herein, a "pharmaceutical composition" refers to a composition suitable for administration to a subject, such as a human, in a therapeutic and/or prophylactic capacity. The pharmaceutical composition comprises an antimicrobial agent, an antiparasitic agent, or both. In some embodiments, the pharmaceutical composition comprises both an antiviral agent, such as favipiravir, and an antiparasitic agent, such as ivermectin. The pharmaceutical agent may further comprise pharmaceutically acceptable excipients, including, but not limited to, binders, diluents, carriers, disintegrants, glidants, lubricants, colorants, sweeteners or flavoring agents, preservatives, antioxidants, fillers, emulsifiers, and surfactants. A "pharmaceutically acceptable" excipient refers to a compound or composition generally considered safe for pharmaceutical use, officially approved by a regulatory agency of a national or state government, or listed in the U.S. Pharmacopoeia or other generally recognized pharmacopoeia for use in animals, particularly humans.

As used herein, the term "treat" (and its corresponding terms "treatment" or "treating") includes palliative and restorative treatment of a subject. The term "palliative treatment" refers to treatment that eases or reduces the effect or intensity of a condition in a subject without curing the condition. The term "restorative treatment" refers to treatment that halts the progression of, reduces the pathologic manifestations of, or entirely eliminates a condition (such as COVID-19 or SARS-CoV-2 infection) in a subject.

As used herein, "subject" may be used interchangeably with "individual" and "patient" and refers to a mammal, preferably a human or a non-human primate, but also includes domesticated mammals (e.g., canine or feline), laboratory mammals (e.g., mouse, rat, rabbit, hamster, or guinea pig), and agricultural animal (e.g., equine, bovine, porcine, or ovine). In certain embodiments, the subject can be human (e.g., adult male, adult female, adolescent male, adolescent female, male child, or female child) under the care of a physician or other health care worker. In other embodiments, the subject may not be under the care of a physician or other health care worker.

II. Compositions

A combination of an antimicrobial agent and an antiparasitic agent is provided herein. The antimicrobial agent may be an antiviral agent. Alternatively, the antimicrobial agent may be an antibacterial agent or an anti-fungal agent. In embodiments where the antimicrobial agent is an antiviral agent, the antiviral agent may be a purine nucleic acid analog and/or an RNA-dependent RNA polymerase inhibitor, including, but not limited to, favipiravir, favipiravir-RTP, remdesivir, and molnupiravir. In a preferred specific embodiment, the antiviral agent is favipiravir. In another embodiment, the antiparasitic agent is an avermectin. The avermectin may be ivermectin, selamectin, doramectin, eprinomectin, and abamectin. In another preferred specific embodiment, the antiparasitic agent is ivermectin. In a specific combination, the antiviral agent is favipiravir and the antiparasitic agent is ivermectin.

In a further embodiment, the antimicrobial agent (e.g., the antiviral agent) and the antiparasitic agent are provided in various doses. In an embodiment, the favipiravir is provided at a dose ranging between approximately 200 mg and approximately 3000 mg. The favipiravir may be delivered in a single daily dose (e.g., QD) or administered over multiple doses throughout the day, such as twice a day (e.g., BID), three times a day (e.g., TID), four times a day (e.g., QID), or more often. In a more particular embodiment, the favipiravir may be provided in a dose of between about 200 mg and about 1200 mg, between about 400 mg and about 1000 mg, between about 600 mg and about 800 mg, between about 1200 mg and about 2400 mg, between about 1400 mg and about 2000 mg, or between about 1600 mg and about 1800 mg. Alternatively, the favipiravir may be administered at a dose of about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, or about 2400 mg. In embodiments where favipiravir may be provided multiple times, the amount of favipiravir administered to the subject may be the same or different.

In a further embodiment, ivermectin may be provided of a dose of about 50 µg/kg, about 60 µg/kg, about 70 µg/kg, about 80 µg/kg, about 90 µg/kg, about 100 µg/kg, about 110

μg/kg, about 120 μg/kg, about 130 μg/kg, about 140 μg/kg, about 150 μg/kg, about 160 μg/kg, about 170 μg/kg, about 180 μg/kg, about 190 μg/kg, about 200 μg/kg, about 210 μg/kg, about 220 μg/kg, about 230 μg/kg, about 240 μg/kg, or about 250 μg/kg. In embodiments where ivermectin may be provided multiple times, the amount of ivermectin administered to the subject may be the same or different.

When used in combination any of the above-referenced doses of favipiravir may be combined with any of the above-referenced doses of ivermectin. In a preferred embodiment, the dose of favipiravir may be between about 1600 mg and about 1800 mg and the dose of ivermectin may be about 150 μg/kg. In another preferred embodiment, the dose of favipiravir may be between about 600 mg and about 800 mg and the dose of ivermectin may be about 150 μg/kg.

The antimicrobial agent (such as an antiviral agent) and the antiparasitic agent may be formulated in a single pharmaceutical composition. The antiviral agent may comprise at least 50% by weight of the total weight of the pharmaceutical composition. In such an embodiment, the antiparasitic agent may comprise less than 50% by weight of the total weight of the composition. Alternatively, the antiparasitic agent may comprise at least 50% by weight of the total weight of the pharmaceutical composition. In such an embodiment, the antiviral agent may comprise less than 50% by weight of the total weight of the pharmaceutical composition. In a still further embodiment, the composition may further comprise a sphingolipid modulator, such as amitriptyline.

In an alternative embodiment, the antimicrobial agent (such as an antiviral agent) and the antiparasitic agent may be provided in separate formulations, such as in a kit. In such an embodiment, the separate formulations of the antimicrobial agent (such as an antiviral agent) and an antiparasitic agent may be administered simultaneously, concurrently (e.g., with the antiviral agent administered immediately before or after the antiparasitic agent) or with a period of time between administrations.

II. Methods

In one embodiment is a method for treating an early-stage infection by a microbe in a subject, such as a virus, comprising the steps of providing a sample from the subject to a lateral flow assay, determining whether subject is infected with the microbe based on the results of the lateral flow assay, and if the subject is determined to be infected with the microbe, treating the subject with an antimicrobial agent, wherein the subject has been exposed to the microbe, is suspected of having been exposed to the virus, or has been in contact with a person exposed to or suspected of being exposed to the virus. In a particular embodiment, the microbe is a virus, such as a coronavirus. In a specific embodiment, the coronavirus is SARS-CoV-2. In an alternative embodiment, the virus may be an influenza virus, SFTS virus, Ebola virus, or Lassa virus.

Alternatively, a method for treating a subject having an early-stage infection by a microbe comprising administering to the subject a combination of an antimicrobial agent and an antiparasitic agent, wherein the early-stage infection is determined by a lateral flow assay is provided. The microbe causing the early-stage infection may be a virus, such as a coronavirus or, specifically, the SARS-CoV-2 virus. In other embodiments, the virus may be an influenza virus, SFTS virus, Ebola virus, or Lassa virus.

In some embodiments, the antiviral agent is a purine nucleic acid analog or, more specifically, an agent that inhibits RNA-dependent RNA polymerase (RDRP). In a specific embodiment, the antiviral agent may include favipiravir, favipiravir-RTP, remdesivir, and molnupiravir. In a preferred embodiment, the antiviral agent is favipiravir. In a specific preferred embodiment, the virus may be the SARS-CoV-2 virus and the antiviral agent may be favipiravir.

In embodiments where the microbial infection is a bacterial infection, the antimicrobial agent would be an antibacterial agent (e.g., an antibiotic). In embodiments where the microbial infection is a fungal infection, the antimicrobial agent would be an antifungal agent.

The amount of favipiravir for treating the SARS-CoV-2 infection is described above. In some embodiments, the method may comprise administration two doses of favipiravir per day. In some embodiments, the two doses of favipiravir on the first day (e.g., the loading doses) may be greater than the doses of favipiravir on subsequent days. In a particular embodiment, the first-day doses of favipiravir may each be between about 1600 mg and about 1800 mg and the doses of favipiravir on subsequent days may each be between about 600 mg and about 800 mg.

In a further embodiment, the method further comprises the step of administering an antiparasitic agent. In a particular embodiment, the antiparasitic agent may be ivermectin, selamectin, doramectin, eprinomectin, and abamectin. In a preferred embodiment, the antiparasitic agent is ivermectin. The amount of ivermectin for treating SARS-CoV-2 is described above. In a particular embodiment, the ivermectin may be administered at a dose of about 150 μg/kg. In a specific embodiment, the first day doses of favipiravir may each be between about 1600 mg and about 1800 mg, the subsequent doses of favipiravir may each be between about 600 mg and about 800 mg, and the dose of ivermectin throughout the course of treatment is about 150 μg/kg.

The antimicrobial agent (such as an antiviral agent) and the antiparasitic agent may be formulated in a single pharmaceutical composition. The antiviral agent may comprise at least 50% by weight of the total weight of the pharmaceutical composition. In such an embodiment, the antiparasitic agent may comprise less than 50% by weight of the total weight of the composition. Alternatively, the antiparasitic agent may comprise at least 50% by weight of the total weight of the pharmaceutical composition. In such an embodiment, the antiviral agent may comprise less than 50% by weight of the total weight of the pharmaceutical composition. In a still further embodiment, the composition may further comprise a sphingolipid modulator, such as amitriptyline.

As mentioned above, the method described herein may be useful for treating a coronavirus infection. More specifically the virus may be the SARS-CoV-2 virus. In such embodiments, the method may comprise administering to the subject an antiviral agent and an antiparasitic agent. In a preferred embodiment, the antiviral agent may be favipiravir and the antiparasitic agent may be ivermectin.

The amount of favipiravir for treating the SAR-CoV-2 infection is described above. In some embodiments, the method may comprise administration two or more doses of favipiravir per day. The two or more doses of favipiravir on the first day (e.g., the loading doses) may be greater than the doses of favipiravir on subsequent days. In a particular embodiment, the first-day doses of favipiravir may each be between about 1600 mg and about 1800 mg and the doses of favipiravir on subsequent days are each between about 600 mg and about 800 mg. The amount of ivermectin for treating SARS-CoV-2 is described above. In a particular embodiment, the ivermectin may be administered at a dose of about 150 µg/kg. Further, the first day doses of favipiravir may each be between about 1600 mg and about 1800 mg, the subsequent doses of favipiravir may each be between about 600 mg and about 800 mg, and the dose of ivermectin throughout the course of treatment may be about 150 µg/kg.

In a particular embodiment, first doses of favipiravir are administered on Day 0 and subsequent favipiravir doses may be administered daily on multiple subsequent days and ivermectin is administered on Day 1 and on multiple subsequent days. For example, a loading dose of favipiravir may be administered on Day 0, and on subsequent doses may be administered on Days 2-30, Days, 2-25, Days 2-20, Days 2-15, Days 2-10, or Days 2-5. Additionally, the ivermectin may be administered on Days 1-60, Days 1-55, Days 1-50, Days 1-45, Days 1-40, Days 1-35, Days 1-30, Days 1-25, Days 1-20, Days 1-20, Days 1-15, Days 1-10, and Days 1-5. In a particular schedule, the favipiravir may be administered on Days 0 (as a loading dose) and on Days 2-5 and ivermectin may be administered on Days 1-10. As described in the above schedule, the favipiravir and ivermectin may be administered on the same day. For each day administered, the favipiravir and/or ivermectin may be administered QD, BID, TID, QID, or more. When the favipiravir and ivermectin are administered on the same day, both agents may be administered simultaneously (e.g., as part of a singular formulation), concurrently (where one agent is administered immediately after the other), or with a period of time between administration of each dose.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

The term "about" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. For example, the terms "generally," "about," and "substantially," may be used herein to mean within manufacturing tolerances. Or for example, the term "about" as used herein when modifying a quantity of an ingredient or reactant of the invention or employed refers to variation in the numerical quantity that can happen through typical measuring and handling procedures used, for example, when making concentrates or solutions in the real world through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about," the claims include equivalents to the quantities.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

With that said, the foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for treating an early-stage infection by a virus in a subject comprising the steps of:
   obtaining a sample from the subject,
   providing the sample to a lateral flow assay,
   determining whether the subject is infected with the virus based on the results of the lateral flow assay, and
   if the subject is determined to be infected with the virus, administering to an antiviral agent and an antiparasitic agent the subject,
   wherein the subject has been exposed to the virus, is suspected of having been exposed to the virus, or has been in contact with a person exposed to or suspected of being exposed to the virus,
   wherein the antiviral agent is selected from the group consisting of favipiravir, favipiravir-RTP, remdesivir, and molnupiravir and the antiparasitic agent is ivermectin, and
   wherein the virus is SARS-CoV-2.

2. The method of claim 1, wherein the antiviral agent is favipiravir.

3. The method of claim 2, wherein the favipiravir is administered at a dose of between about 1600 mg and about 1800 mg or between about 600 mg and about 800 mg and the ivermectin administrated at a dose of about 150 µg/kg.

4. The method of claim 2, wherein the favipiravir and the ivermectin are each administered in a plurality of doses over a plurality of days.

5. The method of claim 4, wherein the favipiravir is administered twice per day, wherein the doses of favipiravir administered on the first day are between about 1600 mg and about 1800 mg, and the doses of favipiravir administered on subsequent days are between about 600 and about 800 mg.

6. The method of claim 4, wherein the ivermectin is administered a daily, wherein a first dose of ivermectin is administered at least one day after a first dose of favipiravir.

7. The method of claim 4, wherein the favipiravir is administered on days 0 and 2-5 and the ivermectin is administered on days 1-10.

8. The method of claim 4, wherein the favipiravir is administered simultaneously with or immediately before or after administration of ivermectin.

9. A method for treating a subject having an early-stage viral infection comprising administering to the subject a combination of an antiviral agent and an antiparasitic agent,
   wherein the early-stage viral infection is determined by a lateral flow assay,
   wherein the antiviral agent is selected from the group consisting of favipiravir, favipiravir-RTP, remdesivir, and molnupiravir and the antiparasitic agent is ivermectin, and
   wherein the virus is SARS-CoV-2.

10. The method of claim 9, wherein the antiviral agent is favipiravir.

11. The method of claim 10, wherein the favipiravir is administered at a dose of between about 1600 mg and about 1800 mg or between about 600 mg and about 800 mg and the ivermectin administrated at a dose of about 150 µg/kg.

12. The method of claim 9, wherein the sample is selected from the group consisting of saliva, blood, plasma, lymph, mucus, urine, feces, cells, and tissues.

\* \* \* \* \*